United States Patent [19]
Rademacher et al.

[11] Patent Number: 5,981,494
[45] Date of Patent: Nov. 9, 1999

[54] USE OF GLYCOSIDASE INHIBITORS

[75] Inventors: Thomas Rademacher, Oxford; John Playfair, London; Hugo Caro, Herts; Janice Taverne; Nadeem Sheikh, both of London, all of United Kingdom

[73] Assignee: University College London, London, United Kingdom

[21] Appl. No.: 09/141,288

[22] Filed: Aug. 27, 1998

Related U.S. Application Data

[63] Continuation of application No. 08/895,091, Jul. 16, 1997, abandoned.

[30] Foreign Application Priority Data

Jan. 8, 1997 [GB] United Kingdom ................. 97002331

[51] Int. Cl.[6] .................................................. A61K 31/70
[52] U.S. Cl. ................................................................ 514/23
[58] Field of Search .................................................. 514/23

[56] References Cited

PUBLICATIONS

Wright et al., *Biochemical Pharmacology* 41(12):1855–1861 (1991).
Caro et al., *Infection and Immunity* 64(8):3438–3441 (1996).

*Primary Examiner*—Raymond Henley, III
*Attorney, Agent, or Firm*—Richard F. Trecartin; Flehr Hohbach Test Albritton & Herbert LLP

[57] ABSTRACT

The present invention is directed to the use of glycosidase inhibitors for inhibiting the conversion of a pro-toxin to a toxin by a glycosidase enzyme. In particular, the present invention relates to the use of glycosidase inhibitors for the treatment of malaria, endotoxic shock or septic shock.

10 Claims, 3 Drawing Sheets

USE OF GLYCOSIDASE INHIBITORS

This application is a continuation of Ser. No. 08/895,091, filed Jul. 16, 1997, now abandoned.

FIELD OF THE INVENTION

The present invention relates to the use of a glycosidase inhibitor in the preparation of a medicament for inhibiting the conversion of a pro-toxin to toxin by a glycosidase enzyme. In particular, the present invention relates to these medicaments and methods of using them in the treatment of malaria, endotoxic shock or septic shock.

BACKGROUND OF THE INVENTION

Since the severity of clinical manifestations of malaria correlates with the presence of tumour necrosis factor a (TNFα) in the circulation (13,8,15), components of parasitized erythrocytes which induce its production and cause hypoglycaemia (25,6,26) are customarily referred to as toxins (11). The TNF-inducing activity is associated with a phospholipid (3,1).

Endotoxins are responsible for initiation of septic shock which increases the number of fatalities in Gram-negative bacteremia. The mortality from septic shock is high despite advances in antibiotic therapy. Endotoxins are lipopolysaccharides (LPS) which are released from the bacteria and induce shock by stimulating the release of endogenous inflammatory mediators including tumour necrosis factor α (TNFα), interleukin 1β (IL-1β), IL-6, IL-8γ-interferon, leukemia inhibitory factor, tissue factor, histamine and nitric oxide. These endogenous mediators act in concert and are either additive or synergistic in their effects. Therefore, therapies designed to inhibit the release or neutralise the activity of single components have shown only modest protection against lethality. LPS interacts with cells by complexing with endotoxin-binding protein and binding CD14, by a pertussis toxin-sensitive p73 receptor, via lectin receptors and by serum-independent hydrophobic mechanisms. The intracellular signalling mechanisms triggered by LPS are not fully elucidated. A therapy which prevents the release of endotoxin from bacteria or was able to neutralise the action of endotoxin before it bound to mammalian cell surfaces would be valuable. At present no effective medicament for either of the above conditions has been developed.

SUMMARY OF THE INVENTION

Malaria toxin causes hypoglycaemia and induction of tumour necrosis factor (TNF). The present inventors have found that the induction of TNF in macrophages by malaria toxin was enhanced by pre-treatment of the toxin with α-galactosidase. Thus, the present invention relates to a new prophylactic or therapeutic treatment of malaria using inhibitors of glycosidase enzymes, such as α-galactosidase to reduce the conversion of the toxin precursor to toxin, thereby reducing the amount of toxin circulating in malaria patients.

The present inventors have also unexpectedly found that bacterial derived endotoxin is also a protoxin. Treatment of bacterial derived LPS with glycosidic enzymes, in particular α-galactosidase, renders LPS 10-100 fold more potent in stimulating the release of TNFα from macrophages. Thus, the present invention relates to new prophylactic or therapeutic treatment of septic shock by inhibiting either bacterial derived glycosidases or glycosidases present in mammalian serum thereby reducing the conversion of the pro-endotoxin to the more active endotoxin.

Thus, the present invention is based on the finding that glycosidase enzymes are involved in the conversion of malaria pro-toxin to toxin and in the induction of septic or endotoxic shock. Accordingly, the present invention concerns the use of glycosidase inhibitors in the treatment of these conditions.

Accordingly, in a first aspect, the present invention provides the use of a glycosidase inhibitor in the preparation of a medicament for inhibiting the conversion of a pro-toxin to toxin by a glycosidase enzyme, wherein the medicament is for the treatment of malaria, endotoxic shock or septic shock.

In a further aspect, the present invention provides a method for treating a patient having malaria, endotoxic shock or septic shock comprising administering to the patient a therapeutically effective amount of a glycosidase inhibitor.

The above use or method of treatment may be prophylactic or therapeutic in nature and both forms of treatment are included within the scope of the present invention.

Preferably, the glycosidase inhibitor is a galactosidase inhibitor, and more preferably is an α-galactosidase inhibitor. A wide variety of α-galactosidase inhibitors are known in the art for the treatment of other conditions and the skilled person could readily employ them in the present invention. An example of one such α-galactosidase inhibitor is deoxygalactonojirimycin (dGJ), commercially available from Oxford Glycosystems Limited, Hitching Court, Abingdon, OX14 1RG.

In the present invention, the term "malaria" defines a range of disorders caused by species of the sporazoan Plasmodium in human or other vertebrate red blood cells (RBC). Preferably, the medicament is used to treat malaria in mammals, more preferably humans.

In the present invention, the terms "septic shock" and "endotoxic shock" include the treatment of shock to a wide variety of pathogenic Gram-negative bacteria including *Escherichia coli* and strains of Salmonella, such as *Salmonella typhimurium*.

The compositions for use in the present invention may comprise, in addition to one or more glycosidase inhibitors, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, lactated Ringer's injection. Preservatives, stabilisers, buffers, antioxidants and/or other additives may be included, as required.

In the present invention, preferably the glycosidase inhibitor(s) are administered in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Aspects of the present invention will now be illustrated with reference to the accompanying figures, by way of example and not limitation. Further aspects and embodiments will be apparent to those of ordinary skill in the art.

Figure 1:
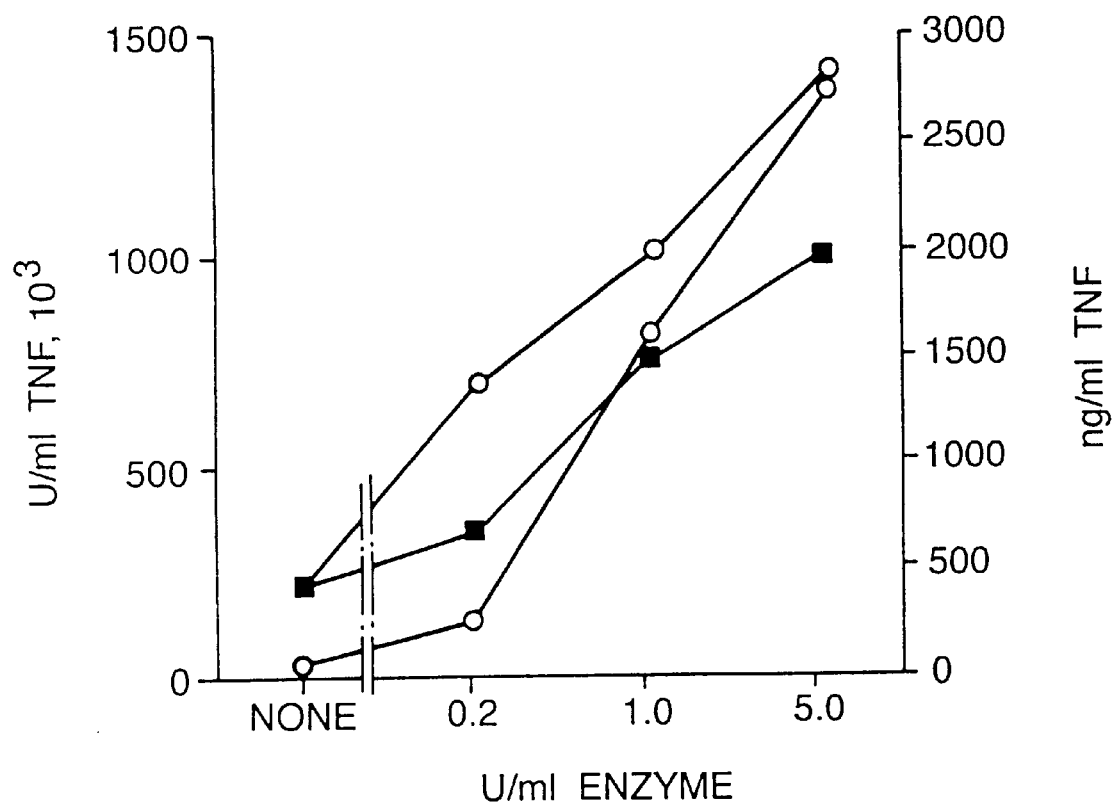
FIG. 1 shows typical enhancement of the TNF-inducing ability of malaria toxin by treatment with α-galactosidase from 2 different sources. Serial dilutions of an extract of parasitized RBC which (undiluted) induced 435 ng/ml of TNF as determined by ELISA and 30,400 U/ml in the bioassay were incubated at pH 8.0 at 37° C. overnight with a series of concentrations of α-galactosidase from Sigma or from Oxford Glycosystems, boiled, neutralised and then tested on macrophages for TNF induction by bioassay and ELISA (means of duplicates). The amount of TNF that would have been induced by the original undiluted extract was then calculated.

○=U/ml by bioassay (enzyme from Sigma).

●=ng/ml by ELISA (enzyme from Sigma).

■=ng/ml by ELISA (enzyme from Oxford GlycoSystems).

FIG. 2 shows the enhancement of TNF-inducing activity of malaria toxin and of LPS at different pH compared with specific α-galactosidase activity. (One of 2 experiments) (A) Rate of reaction of 0.04 U/ml of α-galactosidase at 37° C. with p-nitrophenyl-α-D-galactopyranoside as substrate as determined over the first 3 mins. (B) Malaria toxin from *P. yoelii* diluted 1/10 and (C) 50 ng/ml of LPS were incubated overnight at 37° C. with 2 U/ml of α-galactosidase,then boiled and tested on macrophages for TNF induction, assayed by ELISA. (Means of duplicates).

○=Samples incubated in buffer only, boiled, and then adjusted to neutral pH in RPMI 1640 as pH controls.

●=Samples incubated with enzyme.

DETAILED DESCRIPTION

Structural components of the malaria toxin which affect activity have been inferred from enzymatic and chemical treatments. TNF-induction by malaria toxin is unaffected (3) by treatment with dilute HONO. This resistance to HONO distinguishes the active portion of lipidic TNF-inducing malaria toxin from GPI anchors of proteins which are degraded by HONO, owing to the presence of a non-N-acetylated hexosamine residue.

Glycoconjugates from parasites such as lipophosphoglycans attach to membrane via GPI anchors (16) and the glycan moiety of GPI-anchored proteins from parasites (27) may contain α-galactose residues. Likewise, bacterial lipopolysaccharide (LPS) contains α-galactose residues (20). α-D-galactosidase has also been shown to alter the antigenicity of an antigen in Plasmodium falciparum culture medium (12) which induces TNF (23).

Mice bred at University College London ((CBA×Balb/c) F1 or CBA×C57B1) F1) were infected with *P. yoelii* YM or *P. berghei* ANKA. Parasitized RBC (1×108/ml)in Earle's Balanced Salt Solution (BSS; Life Technologies Ltd, Paisley, U.K.) were incubated at 37° C. overnight, then disrupted by freezing and thawing, digested overnight with 250 μg pronase E (Sigma) per mg of protein (determined by BioRad assay), boiled, treated with 25 μg/ml polymyxin B agarose (Sigma) to eliminate endotoxin, filtered through a 0.2-μm filter (Sartorius AG, Gottingen, Germany) and stored at 4° C. (24). TNF induction from thioglycollate-induced peritoneal macrophages and ELISA assays for murine TNF were described previously (24). Polymyxin B (5 μg/ml) was included in all experiments with malaria toxin to exclude effects from contaminating LPS. A more sensitive one-plate procedure for TNF production and assay was also used (5). Cytotoxicity assays for TNF were done using L929 cells (23). Green coffee bean α-D-galactosidase was obtained from 2 sources (Sigma, Poole, Dorset, UK and Oxford GlycoSystems Ltd, Abingdon, Oxford UK).

Significant increase in TNF-induction in macrophages was reproducibly observed when more than a dozen different extracts of RBC infected with *P. yoelii*, and 3 with *P. berghei* (but not uninfected RBC controls that did not induce TNF) were pre-treated with α-D-galactosidase. A typical titration showing dose-dependent enhancement of TNF induction by one sample of malaria toxin treated with increasing amounts of α-galactosidase is shown (FIG. 1). The amount of TNF enhancement by any concentration of α-galactosidase depended on toxin potency, higher dilutions of toxin always showing greater enhancement. No TNF was induced from macrophages incubated with 2 U/ml enzyme only and no enhancement occurred with boiled enzyme, again excluding any contribution from contaminating LPS, which is heat-stable. Macrophages treated with 2 U/ml of enzyme for 1 hr at 37° C., then stimulated with toxin or 2 or 10 ng/ml of LPS, did not secrete more TNF than untreated cells.

The α-galactosidase hydrolysis of p-nitrophenyl-α-D-galactopyranoside (αPNP-Gal) is optimal at pH 6.0 (4, 9) and undetectable at pH 8.0 (9), as we confirmed, but enhancement of TNF-induction by malaria toxin was greatest at pH 8.0 (FIG. 2.). The TNF-inducing activity of LPS was also enhanced with a similar pH profile to the toxin, indicating a homologous structure/function relationship. The degree of enhancement also varied with the concentration of LPS, and at higher concentrations enhancement was also detectable at pH 6.0.

The most likely explanation for the lack of activity against αPNP-Gal at pH 8.0 is the presence of an α-galactosidase activity which does not hydrolyse this substrate. This was supported by the observation of batch to batch variability and the fact that the stability of the TNF-enhancing activity differed from the αPNP-Gal activity. Although all enzyme preparations were first dialysed and adjusted to the same activity against αPNP-Gal, batches from different sources enhanced to different degrees (as illustrated in FIG. 1). TNF-enhancing capacity deteriorated with storage at 4° C., although activity against the αPNP-Gal substrate did not. No differences were visible in a 10% SDS PAGE mini-gel system (Pharmacia, Uppsala, Sweden), using 4.5 μg of protein, between batches which did or did not enhance. Apart from BSA, all preparations contained 3 bands of 33 kD, 29 kD and 27 kD; 28 kD and 36.5 kD isoforms were previously described (4). No β-galactosidase activity was detectable against βPNP-Gal at pH 6.0, nor did 0.8 U/ml of β-galactosidase (Sigma, Grade X from E.coli), at any pH from 4 to 8, affect malaria toxin or LPS activity.
Figure 2A:
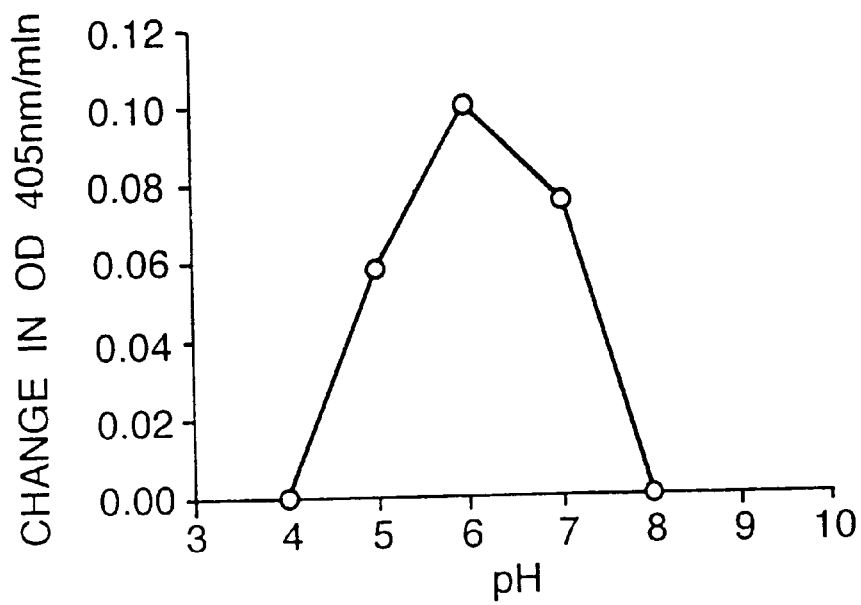
Figure 2B:
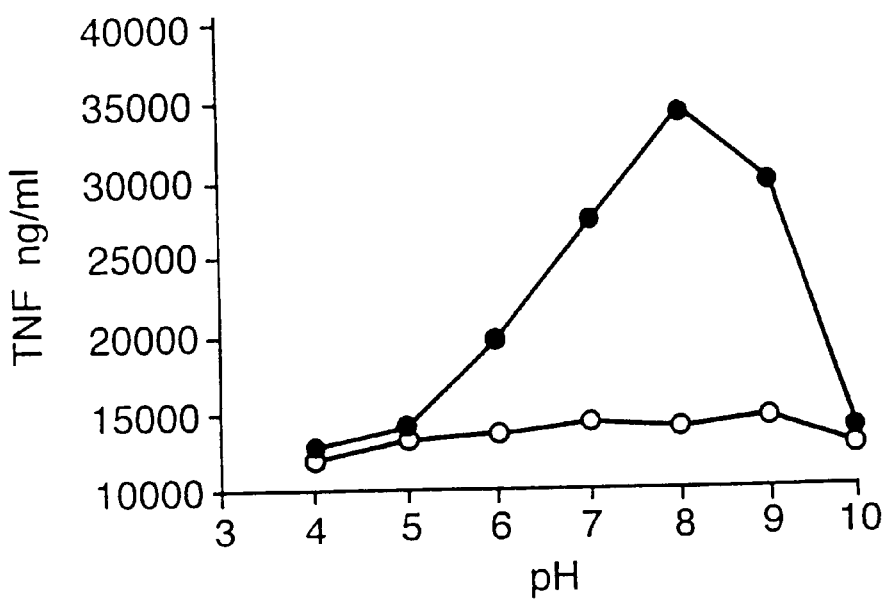
Figure 2C:
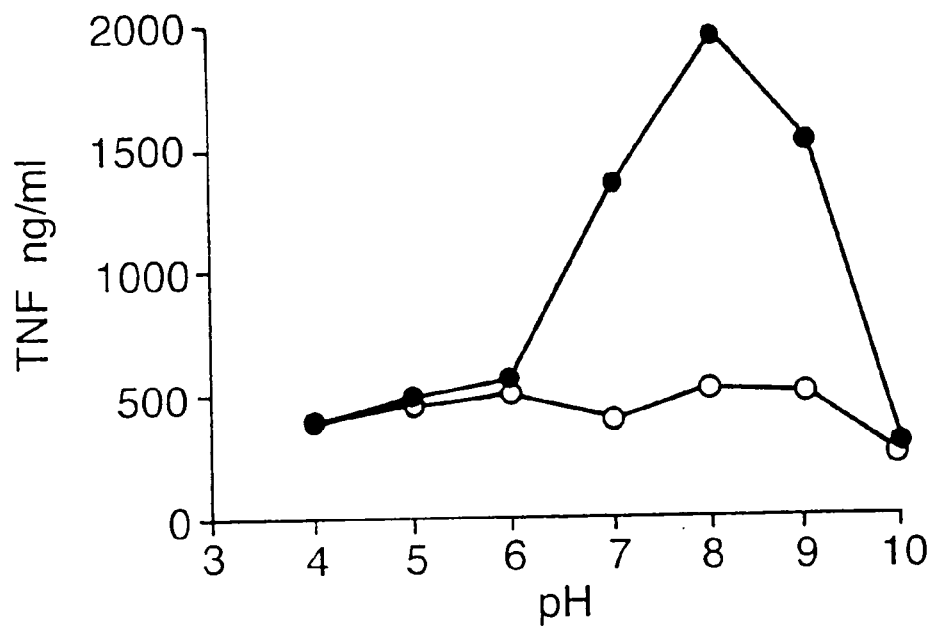

It is commonly found that not all exoglycosidase activities can be monitored using a PNP surrogate substrate. For example, while the α-(1,2), α-(1,3) and α-(1,6) mannosidase activity of jack bean a-mannosidase can be assayed using PNP-mannoside, the α-(1,2) mannosidase activity from Aspergillus phoenicis cannot and only natural substrates can be used (10). This property is normally referred to as the aglycon specificity of an exoglycosidase.

References:

All of the references mentioned herein are incorporated by reference.

1. Bate, C. A. W., and D. Kwiatkowski. 1994. A monoclonal antibody that recognizes phosphatidylinositol inhibits induction of tumor necrosis factor alpha by different strains of Plasmodium falciparum. Infect. Immun. 62:5261–5266.
2. Bate, C. A. W., J. Taverne, E. Romβ, C. Moreno, and J. H. L. Playfair. 1992. TNF induction by malaria exoantigens depends upon phospholipid. Immunology 75: 129–135.
3. Carchon H., and C. K. D. de Bruyne. 1975. Purification and properties of coffee-bean α-D-galactosidase. Carbohydr. Res. 41: 175–189.
4. de Groote, D., Y. Gevaert, M Lopez, R. Gathy, F. Fauchet, I. Dehart, M. Jadoul, D. Radoux, and P. Franchimont. 1993. Novel method for the measurement of cytokine production by a one-stage procedure. J. Immunol. Methods 163: 259–267.
5. Elased, K. and J. H. L. Playfair. 1994. Hypoglycemia and hyperinsulinemia in rodent models of severe malaria infection. Infect. Immun. 62: 5157–5160.
6. Gaulton, G. N., and J. C. Pratt. 1994. Glycosylated phosphatidylinositol molecules as second messenger. Semin. Immunol. 6:97–107.
7. Grau G. E., T. E. Taylor, M. E. Molyneux, J. J. Wirima, P. Vassalli, M. Hommel and P-H. Lambert. 1989. Tumor necrosis factor and disease severity in children with falciparum malaria. N. Eng. J. Med. 320: 158–1591.
8. Haibach, F., J. Hata, M. Mitra, M. Dhar, M. Harmata, P. Sun, and D. Smith. 1991. Purification and characterization of a Coffea canephora α-D-galactosidase isozyme. Biochem. Biophys. Res. Commun. 181: 1564–1571.
9. Ichishima, E., M. Arai, Y. Shigematsu, H. Kumagai, and R Sumida-Tanaka. 1981. Purification of an acidic alpha-D-mannosidase from Aspergillus saitoi and specific cleavage of 1,2-alpha-D-mannosidic linkage in yeast mannan. Biochim. Biophys. Acta. 658: 45–53.
10. Jakobsen, P H., C. A. W. Bate, J. Taverne, and J. H. L. Playfair. 1995. Malaria: toxins, cytokines and disease. Parasite Immunol. 17: 223–231.
11. Jakobsen, P H., T. G. Theander, J. B. Jensen, K. M°lbak, and S. Jepsen. 1987. Soluble Plasmodium falciparum antigens contain carbohydrate moieties important for immune reactivity. Infect. Immun. 25: 2075–2079.
12. Kern, P., C. J. Hemmer, J. van Damme, H-J. Gruss, and M. Dietrich. 1989. Elevated tumor necrosis factor α and interleukin-6 serum levels as markers for complicated Plasmodium falciparum malaria. Am. J. Med. 57:139–143.
13. Kwiatkowski D., A. V. S. Hill, I. Sambou, P. Twumasi, J. Castracane, K. R. Manogue, A. Cerami, D. R. Brewster and B. M. Greenwood. 1990. TNF concentration in fatal cerebral, non-fatal cerebral, and uncomplicated Plasmodium falciparum malaria. Lancet 336: 1201–1204.
14. McConville, M. J., and M. A. J. Ferguson. 1993. The structure, biosynthesis and function of glycosylated phosphatidylinositols in the parasitic protozoa and higher eukaryotes. Biochem. J. 294: 305–324.
15. Raetz, C. R. H. 1990. Biochemistry of endotoxins. Annu. Rev. Biochem., 59: 129–170.
16. Schofield L., and Hackett F. 1993. Signal transduction in host cells by a glycosylphosphatidylinositol toxin of malaria parasites. J. Exp. Med. 177: 145–153.
17. Taverne, J., C. A. W. Bate, D. Kwiatkowski, P. H. Jakobsen, and J. H. L. Playfair. 1990. Two soluble antigens of Plasmodium falciparum induce tumor necrosis factor release from macrophages. Infect. Immun. 58:2923–2928.
18. Taverne, J., N. Sheikh., J. B. de Souza, J. H. L. Playfair, L. Probert, and G. Kollias. 1994. Anaemia and resistance to malaria in transgenic mice expressing human tumour necrosis factor. Immunology 82: 397–403.
19. Taylor K., C. A. W. Bate, R. E. Carr, G. A. Butcher, J. Taverne and J. H. L. Playfair. 1992. Phospholipid-containing toxic malaria antigens induce hypoglycaemia. Clin. Exp. Immunol. 90: 1–5.
20. Taylor K., R. E. Carr, J. H. L. Playfair, and E. D. Saggerson. 1992. Malarial toxic antigens synergistically enhance insulin signalling. FEBS. 311: 231–234.
21. Thomas, J. R., R. A. Dwek, and T. W. Rademacher. 1990. Structure, biosynthesis, and function of glycosylphosphatiylinositols. Biochemistry 29: 5413–5422.
22. Rice, G. C., Brown, P. A., Nelson, R. J., Bianco, J. A., Singer, J. W., and Bursten, S. 1994. Protection from endotoxic shock in mice by pharmacologic inhibition of phosphatidic acid. Proc. Natl. Acad Sci. 91: 3857–3861.

We claim:

1. A method for treating malaria, endotoxic shock or septic shock, said method comprising administering to a mammal a therapeutically or prophylactically effective amount of a glycosidase inhibitor, wherein said qlycosidase inhibitor inhibits the conversion of pro-toxin to toxin which causes malaria, endotoxic shock or septic shock in said mammal.

2. The method of claim 1, wherein the glycosidase inhibitor is a galactosidase inhibitor.

3. The method of claim 2, wherein the galactosidase inhibitor is an α-galactosidase inhibitor.

4. The method of claim 1, wherein the mammal is a human.

5. The method of claim 1, wherein the septic or endotoxic shock is caused by pathogenic gram-negative bacteria.

6. A method of inhibiting the conversion of a pro-toxin to a toxin which causes malaria, endotoxic shock or septic shock in a mammal, said method comprising administering to said mammal a glycosidase inhibitor, wherein the conversion of said pro-toxin to said toxin is inhibited.

7. The method of claim 6, wherein the glycosidase inhibitor is a galactosidase inhibitor.

8. The method of claim 7, wherein the galactosidase inhibitor is an α-galactosidase inhibitor.

9. The method of claim 1, wherein said mammal is a human.

10. The method of claim 1, wherein the septic or endotoxic shock is caused by pathogenic gram-negative bacteria.

* * * * *

UNITED STATES PATENT AND TRADEMARK OFFICE
CERTIFICATE OF CORRECTION

PATENT NO. : 5,981,494

DATED : November 9, 1999

INVENTOR(S) : Rademacher et al.

It is certified that error appears in the above-identified patent and that said Letters Patent is hereby corrected as shown below:

On the title page, item

[75] INVENTORS

Column 1, after the name of the third inventor "Hugo Caro", delete "Herts", and insert therefore --London--.

Column 1, line 17, delete "factor a", and insert therefore --factor α--.

Column 4, line 10, delete "or CBAxC57B1)", and insert therefore --or (CBAxC57B1)--.

Column 5, line 32, delete "M Lopez", and insert therefore --M. Lopez--.

Column 5, line 52, delete "R Sumida-Tanaka", and insert therefore --R. Sumida-Tanaka--

Column 6, line 43, delete "qlycosidase", and insert therefore --glycosidase--.

Signed and Sealed this

Twenty-seventh Day of March, 2001

Attest:

NICHOLAS P. GODICI

Attesting Officer

*Acting Director of the United States Patent and Trademark Office*